United States Patent [19]

Komiya

[11] 4,266,547
[45] May 12, 1981

[54] LASER KNIFE

[75] Inventor: Osamu Komiya, Hachioji, Japan

[73] Assignee: Olympus Optical Co., Ltd., Tokyo, Japan

[21] Appl. No.: 904,468

[22] Filed: Apr. 10, 1978

[30] Foreign Application Priority Data

May 16, 1977 [JP] Japan ................. 52/56634
May 16, 1977 [JP] Japan ................. 52/56636

[51] Int. Cl.³ .......................................... A61B 17/36
[52] U.S. Cl. ................. 128/303.1; 128/395; 128/305; 219/121 LG; 219/121 LV
[58] Field of Search ............... 128/303.1, 395, 305, 128/3, 4, 5, 6, 7, 8, 9, 18, 321, 2 L, 303.13, 303.14, 303.15, 303.16, 303.17, 303.18, 634; 219/121 L, 121 LM, 121 LG, 121 LK, 121 LL, 121 LU, 121 LV, 121 LX, 121 LN; 350/96.26

[56] References Cited

U.S. PATENT DOCUMENTS

| 3,051,166 | 8/1962 | Hounanian ................. 128/4 |
| 3,068,739 | 12/1962 | Hicks et al. ................. 128/6 |
| 3,123,066 | 3/1964 | Brumley ................. 128/634 |
| 3,417,745 | 12/1968 | Sheldon ................. 128/6 |
| 3,762,400 | 10/1973 | McDonald ................. 128/18 |
| 3,821,510 | 6/1974 | Muncheryan ................. 128/303.1 |
| 3,865,113 | 2/1975 | Sharon et al. ................. 128/395 |
| 3,865,114 | 2/1975 | Sharon ................. 128/303.1 |
| 3,942,878 | 3/1976 | Engel et al. ................. 219/121 L |
| 4,011,872 | 3/1977 | Komiya ................. 128/321 |
| 4,020,319 | 4/1977 | Shepard et al. ................. 219/121 LM |

FOREIGN PATENT DOCUMENTS 2207387  8/1973  Fed. Rep. of Germany ........ 128/303.1
7535893  3/1976  Fed. Rep. of Germany .
2543727  4/1977  Fed. Rep. of Germany .
2271802  12/1975 France .

OTHER PUBLICATIONS

Walbarsht, *Laser Applications in Medicine and Biology*, vol. 2. ©1974, Plenum Press, New York, N.Y., pp. 304-305.

*Primary Examiner*—Robert W. Michell
*Assistant Examiner*—Arthur S. Rose
*Attorney, Agent, or Firm*—Weinstein & Sutton

[57] ABSTRACT

A laser knife comprises a tubular member adapted to be inserted into the coeloma by passing through the forceps channel of an endoscope, a laser radiation emitter and acceptor disposed in opposing relationship with each other on the distal end of the tubular member, a laser radiation transmission member for conveying laser radiation to the emitter, a laser oscillator for supplying laser radiation to the transmission member for the purpose of cauterizing an affected part, and means for conveying laser radiation impinging on the acceptor to the outside of a physical body subsequent to the completion of cautery.

36 Claims, 19 Drawing Figures

LASER KNIFE

BACKGROUND OF THE INVENTION

The invention relates to a laser knife, and more particularly to a laser knife which utilizes radiation for cautery of an affected part located within the coeloma for purpose of excision or coagulation.

The prior art practice to incise or excise an affected part located within the coeloma such as a polyp has been by the use of an excision or incision knife which is inserted into the forceps channel of an endoscope, formed by a flexible tube adapted to be inserted into the coeloma, in a manner such that the knife is movable out of or into the distal end of the tube. However, the use of such means requires a high level of skill and is also time consuming. In addition, additional treatments such as stanching or sterilization is required, resulting in a tremendous operation.

There has been an attempt to utilize laser radiation for purpose of excision or incision of an affected part by cauterizing it with such radiation. This removes the necessity for the treatments such as stanching or sterilization. However, as is well recognized, the very high intensity of laser radiation involves the risk that normal tissues other than the affected part may be cauterized or pierced by laser radiation after the intended part has been cauterized. However, it will be appreciated that the use of laser radiation achieves a surgical operation such as incision or excision in a simple manner and within a reduced time, provided provision is made to avoid unintended irradiation of other parts with laser radiation.

SUMMARY OF THE INVENTION

It is a first object of the invention to provide a laser knife which avoids the disadvantages of the prior art by utilizing laser radiation which is directed to an affected part to cauterize it for purpose of excision or incision and in which provision is made for the radiation to be conveyed out of the physical body subsequent to the completion of the cautery.

It is a second object of the invention to provide a laser knife including a laser radiation emitter located on one of a pair of holders, adapted to hold an affected part sandwiched therebetween, and also including a laser radiation acceptor located on the other holder to hold the affected part firmly during the irradiation of the part with laser radiation, and in which the laser radiation is led to the outside of the physical body subsequent to the completion of the cautery, thus avoiding unwanted irradiation of normal tissues.

It is a third object of the invention to provide a laser knife in which laser radiation is directed to an affected part from the opposite sides thereof concurrently.

In accordance with the invention, an affected part which is to be cauterized is irradiated with laser radiation while viewing the part with an endoscope. The cautery of the part with laser radiation takes place for the incision or excision without requiring treatments such as stanching or sterilization, whereby a surgical operation is completed in a reduced time. The operation of the apparatus does not require any significant level of skill, but can be achieved in a simple manner, thus avoiding the disadvantages of the prior art. After the cautery of the affected part, the laser radiation is entirely conveyed to the outside of the physical body, thus removing the risk that normal tissues other than the intended part may be cauterized.

During the irradiation, the affected part is firmly held between a pair of holders, thus assuring the proper alignment of the laser radiation. In addition, it is also possible to direct the laser radiation to an affected part from the opposite sides thereof. Therefore, the irradiation of the part with laser radiation only occurs momentarily, completing the operation in a very reduced length of time.

DESCRIPTION OF PREFERRED EMBODIMENTS

Essentially, the laser knife according to the invention comprises a tubular member adapted to pass through the forceps channel of an endoscope, at least one laser radiation transmission member passing through the tubular member and conveying laser radiation, means on the distal end of the tubular member for forming a laser radiation emitter and an acceptor which are optically opposite one another, and a laser oscillator for supplying laser radiation to the transmission member.

Figure 1:
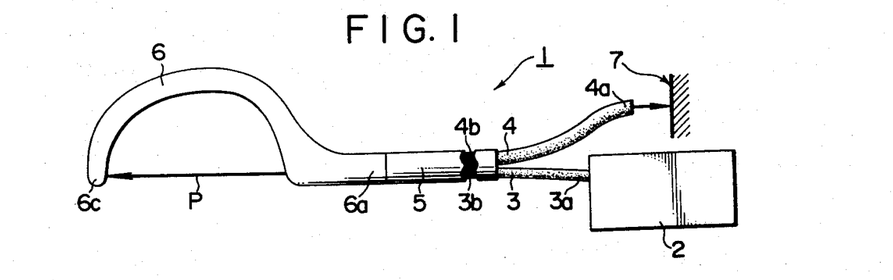
FIG. 1 is a plan view of a laser knife according to one embodiment of the invention.

FIG. 1 shows a laser knife 1 according to one embodiment of the invention. It comprises a laser oscillator 2 which produces laser radiation used to cauterize an affected part. It also comprises a first laser transmission member 3 which conveys the laser radiation to a laser radiation emitter to be described later, and a second laser radiation transmission member 4 having a laser radiation acceptor which is located opposite the emitter and on which laser radiation impinges subsequent to the completion of the cautery. The transmission members 3, 4 pass through a tubular member 5, the distal end of which is fixedly connected with a tube 6 which is adapted to surround an affected part and in which the emitter and the acceptor are disposed in optical alignment with each other. Each of the transmission members 3, 4 may comprise a bundle of optical fibres, for example, and the tubular member 5 is a flexible tube which is inserted into the forceps channel of an endoscope.

Figure 2:
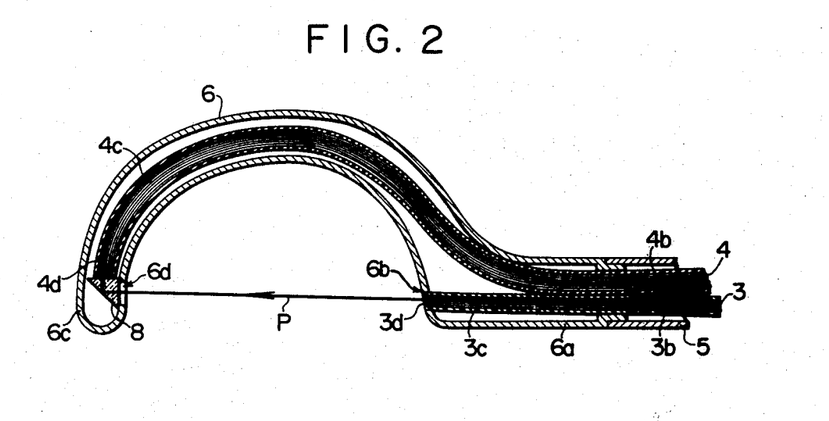
FIG. 2 is a fragmentary cross section, to an enlarged scale, of the laser knife of FIG. 1.

One end 3a of the transmission member 3 is detachably connected with the oscillator 2, and a free length 3b thereof freely passes through the tubular member 5, with its distal end portion 3c (see FIG. 2) extending through a straight portion 6a of an arcuate tube 6 connected with the distal end of the tubular member 5 so that an emitter 3d formed at the extremity of the transmission member is situated within an opening 6b of the tube portion 6a (see FIG. 2). The opening 6b is aligned with the optical axis of the transmission member, and laser radiation P exiting the emitter 3d is directed to the inside of a distal end 6c of the tube 6 along a rectilinear path.

The second transmission member 4 has a portion 4c adjacent to its free end which extends through the arcuate tube 6. The remaining length 4b of the transmission member extends through the tubular member 5 in juxtaposed relationship with the free length 3b of the first transmission member 3, with its opposite end 4a extending out of the tubular member and oriented toward a guard member 7 which may be safely irradiated with laser radiation. The end face of the portion 4c is formed as a laser radiation acceptor 4d, which as shown in FIG. 2, is disposed in abutment against one face of a right-angled prism 8, the other face of which is located in an opening 6d formed in the inside of the distal end 6c of the tube 6. The bundle of optical fibres which forms the second transmission member 4 has a diameter greater than that of the first transmission member 3 so that all of the flux of laser radiation exiting the emitter 3d can impinge on the acceptor 4d even in the presence of a certain degree of optical inclination or misalignment of the end faces of the elements 3, 4.

The tubular member 5 and tube 6 are inserted into a flexible tube 9 (see FIG. 3) of an endoscope, of either direct or lateral view type, which is adapted to be inserted into the coeloma, so as to be movable out of or into the distal end 9a of the flexible tube 9.

Figure 3:
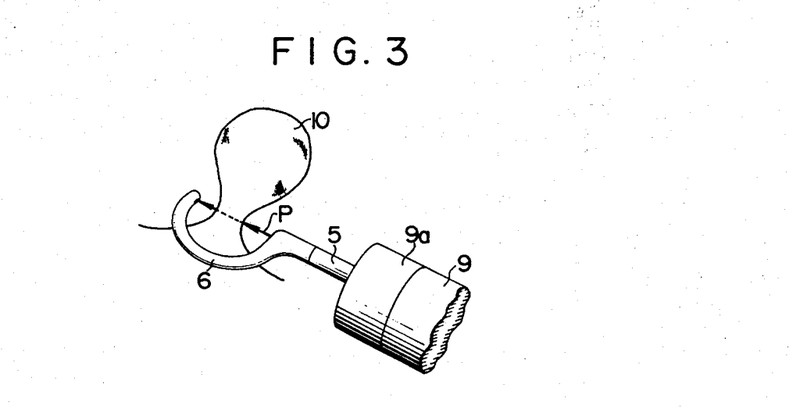
FIG. 3 is a perspective view illustrating the use of the laser knife to excise a polyp located within the coeloma.

FIG. 3 shows the use of the laser knife to excise an affected part located within the coeloma, such as a polyp, for excision thereof. As shown, the tube 6 is extended out of the distal end 9a, and while observing polyp 10 located within the coeloma with the endoscope, it is caused to surround polyp 10 so that the emitter 3d is directed to an intended part such as the base of polyp 10 which is to be cauterized with laser radiation. Subsequently the oscillator 2 may be turned on to supply laser radiation. Thereupon, laser radiation P is conveyed through the first transmission member 3 and is emitted from the emitter 3d to irradiate the base of polyp 10, which is therefore cauterized and excised. Subsequent to the excision of polyp 10, laser radiation from the emitter 3d impinges upon the acceptor 4d through the opening 6d and prism 8, and is thence conveyed to the outside of the body toward the guard member 7 through the second transmission member 4. In this manner, the excision of an affected part such as a polyp can be simply achieved with the laser knife 1 of the invention.

Figure 4:
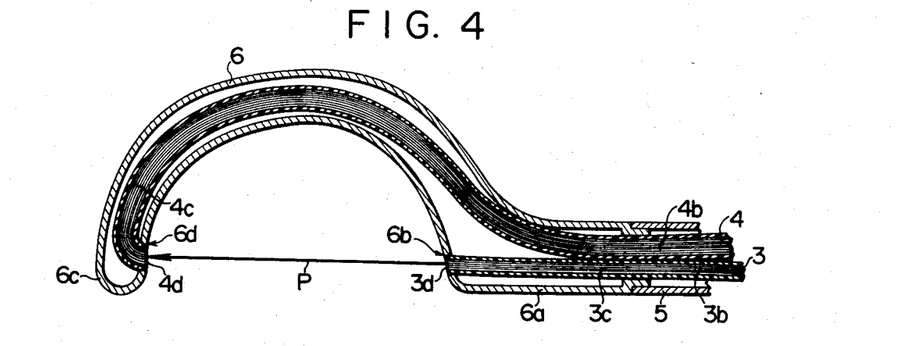
FIG. 4 is a fragmentary enlarged cross section of another form of laser radiation emitter and acceptor.

FIG. 4 shows a modification of the laser knife 1. It will be seen that the prism 8 is removed, and utilizing the flexibility of the optical fibres, the acceptor 4d is directly disposed in the opening 6d.

Figure 5:
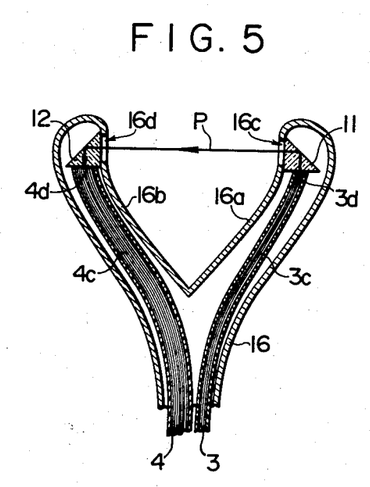
FIGS. 5 and 6 are fragmentary enlarged cross-sectional views of laser knives constructed according to other embodiments of the invention.

FIG. 5 shows another embodiment of the invention in which a tube 16 which surrounds an affected part is V-shaped in section, including a pair of branch tubes 16a, 16b. Adjacent to the free end, the oppositely located inner faces of these branch tubes are formed with openings 16c, 16d, respectively, in which one face of right-angled prisms 11, 12 is disposed. The other face of the prism 11 is located opposite to the emitter 3d of the first transmission member 3 while the other face of prism 12 is located opposite to the acceptor 4d of the second transmission member 4. It will be seen that the laser radiation P is emitted and travels in a direction perpendicular to the length of the transmission members even though it travels along the optical axis of the transmission member 3 in the previous embodiment.

Figure 6:
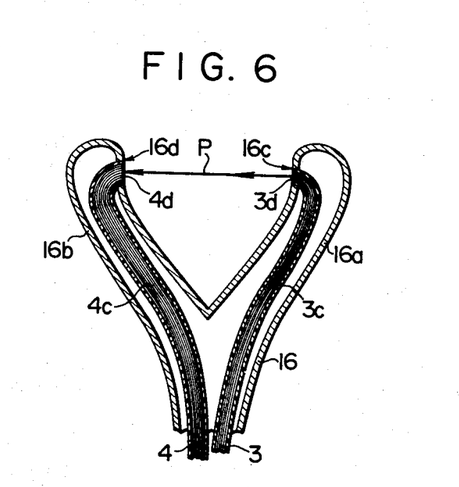

FIG. 6 shows another embodiment in which the flexibility of the optical fibres is utilized to place the emitter 3d and acceptor 4d directly in the openings 16c, 16d, thus removing the prisms 11, 12. This arrangement serves to reduce the manufacturing cost of the apparatus.

Figure 7:
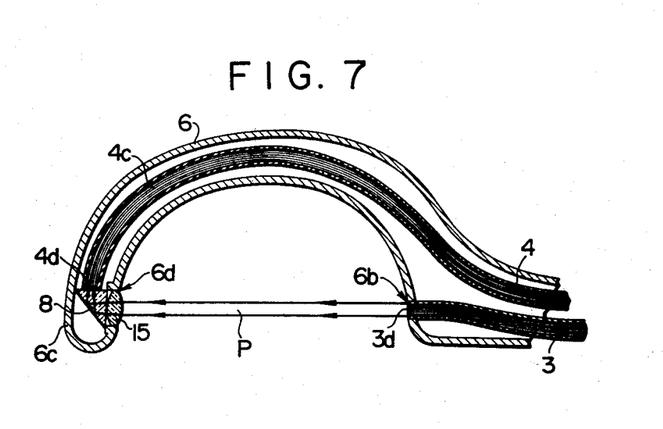
FIG. 7 is a fragmentary cross-section of a further form of a laser radiation emitter and acceptor.

FIG. 7 shows another form of the emitter and acceptor. A convex lens 15 having a lens aperture which assures a sufficient collection of laser radiation P is disposed in the opening 6d in order to assure the impingement of the entire laser radiation P which exits from the emitter 3d. This permits a compact construction of the laser knife without increasing the diameter of the second transmission member 4.

Figure 8:
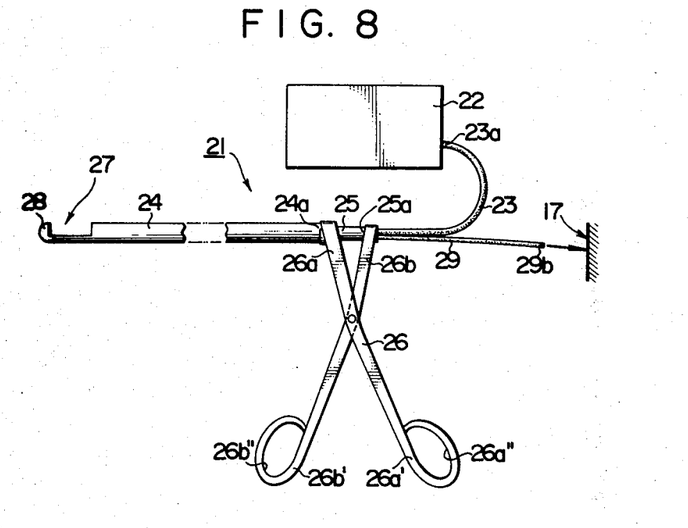
FIG. 8 is a plan view of a laser knife constructed according to another embodiment of the invention.

FIG. 8 shows a laser knife 21 according to a further embodiment of the invention. A laser oscillator 22 supplies laser radiation which is introduced into a first laser radiation transmission member 23, which may comprise a bundle of optical fibres, for example. One end 23a of the transmission member 23 is detachably coupled with the oscillator 22. The transmission member extends through a flexible retainer member 25 to be integrally supported thereby, and its distal end 23b (see FIG. 9) is formed as a laser radiation emitter 23c, which directs the laser radiation conveyed through the transmission member 23 to an affected part to be cauterized for irradiation thereof. It should be noted that the emitter 23c serves as one of holders which hold an affected part sandwiched therebetween emitter 23c and acceptor 29a.

Figure 9:
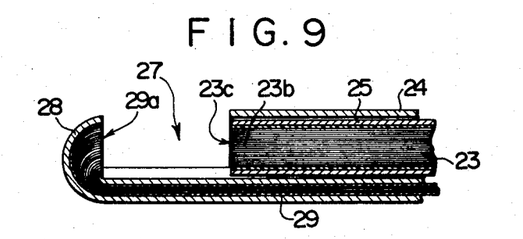
FIG. 9 is a fragmentary enlarged cross-section of the laser knife shown in FIG. 8.
Figure 10:
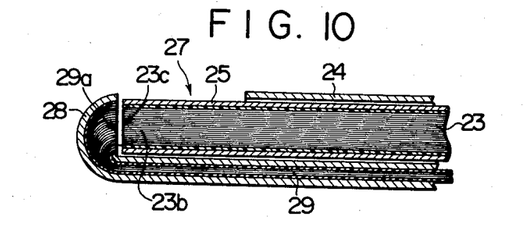
FIG. 10 is a fragmentary cross-section of the part shown in FIG. 9 when it is closed.

Retainer member 25 is freely movable within a tubular member 24, the distal end 28 of which is semi-spherical in configuration, defining a recess 27 for receiving an affected part therein between it and the emitter 23c. Thus, the inner wall of the distal end 28 which faces the recess 27 is disposed opposite to the emitter 23c. A second laser radiation transmission member 29 which extends through the tubular member 24 has its distal end disposed in the inner wall of distal end 28 to define a laser radiation acceptor. The acceptor 29a serves as the other holder. The other end of the transmission member 29 extends out of the proximate end 24a of the tubular member 24, and is disposed as shown at 29b as directed toward a laser radiation guard member 17. The proximate ends 24a, 25a of the tubular member 24 and retainer member 25 are respectively fixedly connected with one end 26a, 26b of a pair of arms which are pivotally connected in a manner to form a scissor-like operating member 26. At its opposite end 26a', 26b', the arms are formed with finger receiving loops 26a'', 26b''. When the ends 26a', 26b' are moved toward each other, the ends 26a, 26b also move toward each other, retracting tubular member 24 connected with the end 26a and moving the retainer member 25 connected with the end 26b forwardly within the tubular member 24. In the position shown in FIG. 8, when the scissors are open, the emitter 23c is spaced from the acceptor 29a as shown in FIG. 9. However, when the scissors are closed, the emitter 23c moves into abutment against the acceptor 29a as shown in FIG. 10.

Figure 11:
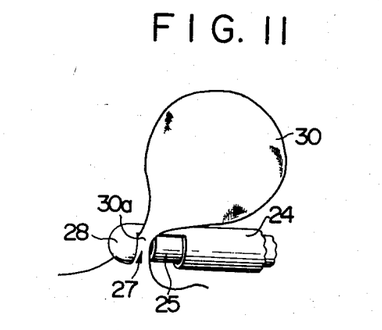
FIG. 11 is a perspective view illustrating the use of the laser knife shown in FIG. 8 in excising a polyp located within the coeloma.

FIG. 11 shows the use of the laser knife 21 to cauterize an affected part such as a polyp located within the coeloma for excision thereof. The tubular member 24 is inserted into the forceps channel of an endoscope 9 as shown in FIG. 1, and while observing the polyp with the endoscope, the members 24, 25 are operated to bring the base 30a of polyp 30 into the recess 27 as shown in FIG. 11. Thereafter, the operating member 26 is operated to hold the affected part sandwiched between the pair of holders, namely, between the emitter 23c and the acceptor 29a. The oscillator 22 can then be turned on, whereby laser radiation is emitted from the emitter 23c to irradiate and cauterize the base 30a, excising polyp 30 in a reduced time. After the completion of the excision, laser radiation now impinges on the acceptor 29a and is then conveyed through the second transmission member 29 and directed toward the guard member 17, thus avoiding the likelihood that normal tissues located within the coeloma may be inadvertently irradiated with laser radiation.

Figure 12:
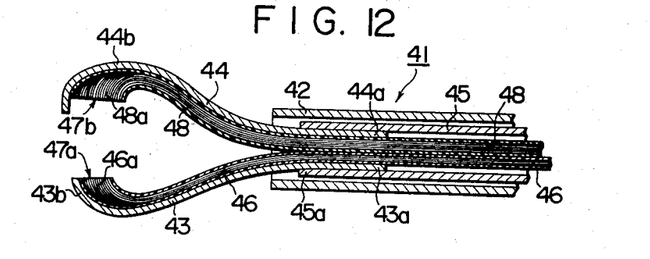
FIG. 12 is a fragmentary enlarged cross-section of a laser knife according to a further embodiment of the invention, particularly illustrating the holders thereof.
Figure 13:
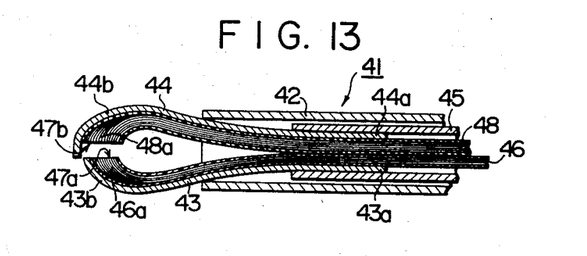
FIG. 13 is a similar cross-section illustrating the holders of FIG. 12 in their closed position.

FIGS. 12 and 13 show another embodiment of the invention in which a laser knife 41 includes holders which are adapted to move in a direction perpendicular to the axis of a tubular member 42 when they are opened or closed. A tubular retainer member 45 is freely movable within the tubular member 42 and has its distal end fixedly connected with one end 43a, 44a of a pair of holding members 43, 44 which are adapted to hold an affected part sandwiched therebetween. The holding member 43 comprises an elongated resilient strip having its free end 43b shaped like a spoon. The other holding member 44 has its free end 44b located opposite to the end 43b of the member 43 so as to cover the latter when both members are brought together (see FIG. 13).

A first and a second laser radiation transmission member 46, 48 have their distal ends 46a, 48a disposed on the free ends 43b, 44b. The transmisson members 46, 48 pass through the retainer member 45 and are separated from each other at the distal end thereof to be supported by the respective holding members 43, 44. The end faces of these transmission members are formed as a laser radiation emitter 47a and a laser radiation acceptor 47b, respectively, which are disposed opposite to each other, and which also serve as holders for holding an affected part sandwiched therebetween. The holding members 43, 44 extend out of the distal end of the tubular member 42 and are normally biased apart. By moving either one of the tubular member 42 and the retainer member 45, the holders can be closed as shown in FIG. 13. Means for effecting such movement can be constructed in a manner similar to that shown in FIG. 8 except for the formation of the holders.

With this arrangement, the capability of the holding members 43, 44 to move in a direction perpendicular to the axis of the tubular member 42 enables an affected part of greater volume to be easily encompassed. An affected part can be properly and firmly held while observing it with an endoscope, facilitating the necessary operation and enhancing the safety even if the knife is remotely operated within a limited space.

Figure 14:
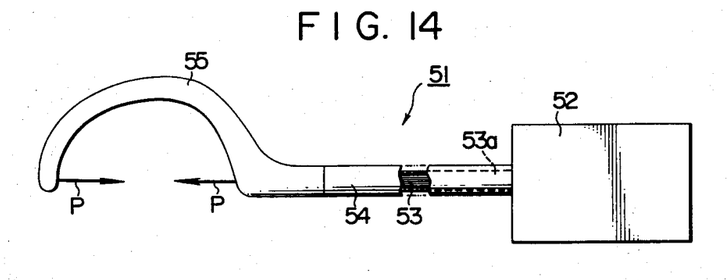
FIG. 14 is a plan view of a laser knife according to still another embodiment of the invention.

FIG. 14 shows a laser knife 51 including a laser oscillator schematically shown at 52 which introduces laser radiation P into a single laser radiaton transmission member 53, which may comprise a bundle of optical fibres, for example. The transmission member 53 passes through a tubular member 54 which is adapted to be inserted into the coeloma of a human body. The member 53 has a proximate end 53a which is detachably coupled with the oscillator 52, and includes a free length 53b (see FIG. 15) extending through the tubular member 54. The distal end of the transmission member is split into two parts 53c, 53d, both of which are disposed within an arcuate tube 55 secured at its one end 55a to the distal end of the tubular member 54 and which are adapted to be used so as to surround an affected part.

Figure 15:
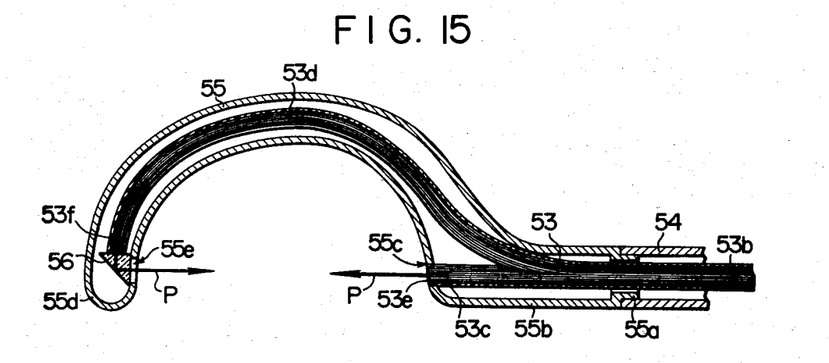
FIG. 15 is a fragmentary enlarged cross-section of part of the laser knife of FIG. 14 which is used to surround and hold an affected part.

The part 53c is disposed within the straight base end 55b of the arcuate tube, and has its distal end disposed in an opening 55c formed in the latter to form a laser radiation emitter 53e. The opening 55c is aligned with the optical axis of the part 53c of the transmission member. An opening 55e is formed in the inside wall of the opposite end 55d of the tube 55 and is located opposite to, or in optical alignment with, the opening 55c. The other part 53d of the transmission member extends through the arcuate tube 55 and terminates short of the free end 55d thereof so as to have its end face held in abutment against one face of a right-angled prism 56, the other face of which is disposed in the opening 55e, whereby the end face forms a laser radiation acceptor 53f. In this manner, an optical communication is established between the end faces of the parts 53c, 53d of the transmission member.

Figure 16:
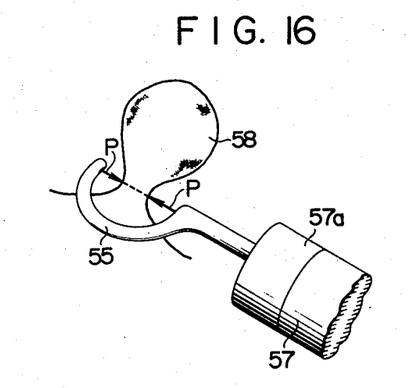
FIG. 16 is a perspective view illustrating the use of the laser knife of FIG. 14 in excising a polyp located within the coeloma.

In use, the tubular member 54 and the arcuate tube 55 are inserted into a flexible tube 57 of an endoscope of either direct or lateral view type (see FIG. 16) so that the arcuate tube 55 can be extended out of or into the distal end 57a of the flexible tube. As shown in FIG. 16, the tube 55 is located, while observing an affected part such as a polyp 58 located within the coeloma with the endoscope, so as to surround the polyp 58 in a manner such that the openings 55c, 55e are located on oppposite sides of the part to be cauterized. The laser oscillator 52 may then be turned on to supply laser radiation to the transmission member 53. Thereupon laser radiation P is simultaneously emitted from the emitters 53e, 53f to irradiate the polyp, which is therefore cauterized and excised within a reduced time, almost instantaneously.

Subsequent to the completion of excision of the polyp, the optical alignment of the parts 53c, 53d permit the laser radiation leaving one of the emitters 53e, 53f to impinge on the other emitter, thus avoiding unwanted irradiation of adjacent tissues and hence assuring a rapid remedy of surrounding tissues.

Figure 17:
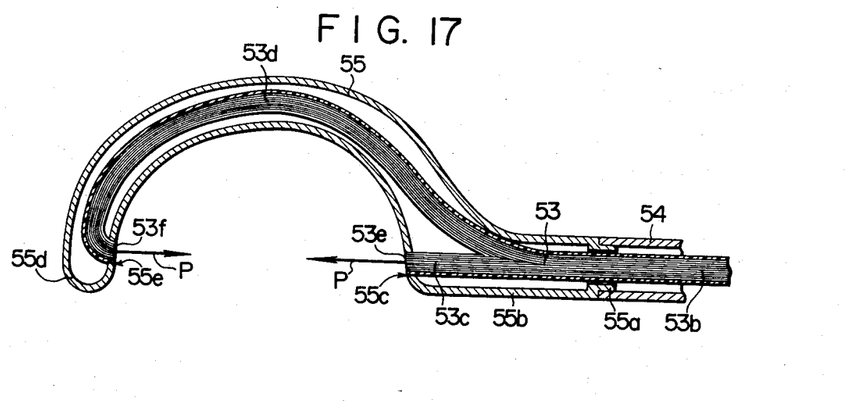
FIG. 17 is a fragmentary enlarged cross-section showing still another form of laser radiation emitter.

FIG. 17 shows a modification of the embodiment shown in FIG. 15 in which the right-angled prism 56 is dispensed with by bringing the emitter 53f directly into the opening 55e which is made possible by the flexibility which a bundle of optical fibres exhibits. The manufacturing cost is thereby reduced accordingly.

Figure 18:
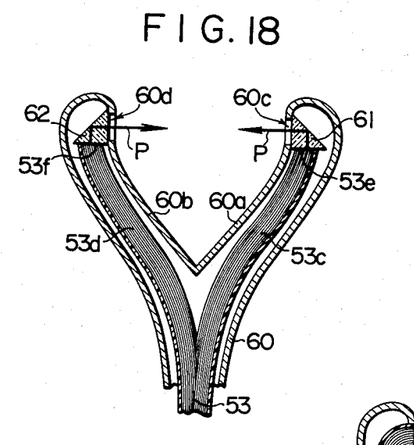
FIGS. 18 and 19 are fragmentary enlarged cross-sections of laser knives according to other embodiments of the invention.

FIG. 18 shows another embodiment of the invention which employs a V-shaped tube 60 for surrounding an affected part. The tube includes a pair of branches 60a, 60b, the opposing inner walls of which are formed with openings 60c, 60d adjacent to their end. A pair of right-angled prisms 61, 62 each have their one face disposed in the respective openings while their other face is disposed in abutment against the end face of respective split parts 53c, 53d of the laser radiation transmission member 53, thus forming emitters 53e, 53f. In this embodiment, it will be seen that laser radiation P travels along a direction which is perpendicular to the optical axis of the transmission member 53 even though it travelled along the optical axis in the embodiments shown in FIGS. 14 to 17.

Figure 19:
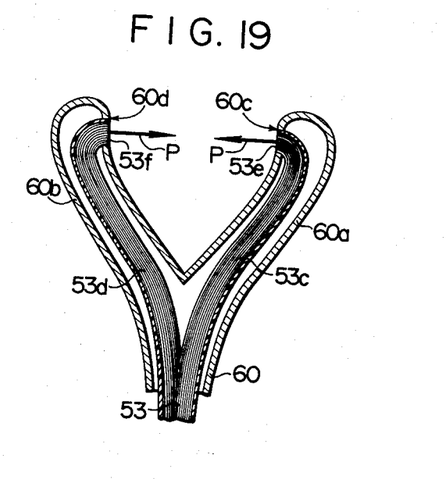

FIG. 19 shows a modification of the arrangement of FIG. 18 in that the use of prisms 61, 62 is avoided in the same manner as in FIG. 17.

In the embodiments described above, the laser radiation transmission members 3, 4, 23, 29, 46, 48, 53 have been described as constructed by a bundle of optical fibres. However, it should be understood that they can be constructed with a glass or plastic rod, liquid fibre or any other material which is capable of conveying laser radiation.

What is claimed is:

1. A laser knife comprising a tubular member having a first end and a second end, said second end of said tubular member being adapted to be inserted into the forceps channel of an endoscope which is to be inserted into a physical body, so that said first end of said tubular member can remain outside of said physical body upon insertion of said endoscope into said physical body, first laser radiation transmission means having a first end and a second end and being continuous therebetween, a laser oscillator for supplying laser radiation to said first laser radiation transmission member, said laser oscillator being capable of emitting a beam with power sufficient to cauterize human tissue, said first laser radiation transmission means being disposed within said tubular member for conveying laser radiation uninterruptedly between said first end of said first laser radiation transmission means and said second end of said first laser radiation transmission means, said second end of said first laser radiation transmission means being disposed at said second end of said tubular member and said first end of said first laser radiation transmission means being disposed at said first end of said tubular member, and second laser radiation transmission means having a first end and a second end and being continuous therebetween, said second laser radiation transmission means being disposed within said tubular member for conveying laser radiation uninterruptedly between said first end of said second laser radiation transmission means and said second end of said second laser radiation transmission means, said second end of said second laser radiation transmission means being disposed at said second end of said tubular member and said first end of said second laser radiation transmission means being disposed at said first end of said tubular member, said second end of said first laser radiation transmission means being disposed in optical alignment with said second end of said second laser radiation transmission means so that laser radiation can be transmitted therebetween.

2. The laser knife of claim 1 including means associated with said first end of said tubular member for discharging laser radiation emitted from said first end of said tubular member.

3. The laser knife of claim 1 wherein said second end of said tubular member includes a non-linear end portion, said second end of said first laser radiation transmission means being disposed at a first point on said non-linear end portion of said tubular member, and said second end of said second laser radiation transmission means being disposed at a second point on said non-linear end portion of said tubular member.

4. The laser knife of claim 3 wherein said second point on said non-linear end portion of said tubular member is located proximate to said second end of said tubular member and said first point on said non-linear end portion of said tubular member is located distal from said second end of said tubular member.

5. The laser knife of claim 4 wherein said non-linear end portion of said tubular member is arcuate.

6. The laser knife of claim 3 wherein said non-linear end portion of said tubular member comprises a V-shaped end portion including two ends, said second point on said non-linear end portion of said tubular member being located at one of said ends of said V-shaped portion of said tubular member and said first point on said non-linear end portion of said tubular member being located at said other end of said V-shaped portion of said tubular member.

7. The laser knife of claim 1 wherein said second end of said first laser radiation transmission means has a greater area than said second end of said second laser radiation transmission means.

8. The laser knife of claim 1 including retainer means carrying said second end of said first laser radiation transmission means, said retainer means being axially movable between first and second positions within said tubular member so that said second end of said first laser radiation transmission means can be moved between said first and second positions by axially moving said retainer means between said first and second positions in said tubular member, said first position being adjacent to said second end of said second laser radiation transmission means and said second position being displaced from said second end of said second laser radiation transmission means, so that when said second end of said first laser radiation transmission means and said second end of said second laser radiation transmission means are near said first position with respect to each other they serve as holders for holding an affected part therebetween.

9. The laser knife of claim 8 including displacing means for axially moving said retainer means with respect to said tubular member.

10. The laser knife of claim 9 wherein said displacing means includes a first arm affixed to said tubular member and a second arm affixed to said retainer means, said first and second arms being pivotally connected to each other.

11. The laser knife of claim 1 including retainer means carrying said first and second laser radiation transmission means, said retainer means being axially movable in first and second directions within said tubular member, first and second holding members carried by said retainer means, said first holding member being associated with said first laser radiation transmission means and said second holding member being associated with said second laser radiation transmission means, said first and second holding members being biased apart so that when said retainer means is axially moved in said first direction, said tubular member causes said first and second holding members to be urged together against said bias.

12. The laser knife of claim 11 including means associated with said first end of said tubular member for discharging laser radiation emitted from said first end of said tubular member.

13. The laser knife of claim 1 wherein said laser oscillator is coupled to said first and second laser radiation transmission means.

14. The laser knife of claim 13 wherein said second end of said tubular member includes a non-linear end portion, said second end of said first laser radiation transmission means being disposed at a first point on said non-linear end portion of said tubular member and said second end of said second laser radiation transmission means being disposed at a second point on said non-linear end portion of said tubular member.

15. The laser knife of claim 14 wherein said second point and said first point are spaced from said second end of said tubular member.

16. The laser knife of claim 15 wherein said non-linear end portion of said tubular member is arcuate.

17. The laser knife of claim 14 wherein said non-linear end portion of said tubular member comprises a V-shaped end portion including two ends, said second point on said non-linear end portion of said tubular member being located at one of said ends of said v-shaped portion of said tubular member and said first point on said non-linear end portion of said tubular member is located at said other end of said V-shaped portion of said tubular member.

18. The laser knife of claim 13 wherein said second laser radiation transmission member has a greater cross-sectional area than said first laser radiation transmission member.

19. The laser knife of claim 1 wherein said first laser radiation transmission means and said second laser rotation transmission means comprise a plurality of fiber optic members.

20. The laser knife of claims 1 or 13 including prism means associated with both said first laser radiation transmission means and said second laser radiation tramsmission means for mounting said first and second laser radiation transmission means in optical alignment with each other.

21. A laser knife comprising a tubular member adapted to be inserted into the forceps channel of an endoscope, said tubular member including a first end and a second end, said second end of said tubular member including a first end location and a second end location in optical alignment with each other and forming a gap therebetween sufficient to receive human tissue, first laser radiation transmission means disposed within said tubular member, said first laser radiation transmission means having a first end and a second end and being continuous therebetween so that laser radiation can be uninterruptedly transmitted therebetween, a laser oscillator, said first end of said first laser radiation transmission means being arranged to receive laser radiation from said laser oscillator sufficient to cauterize human tissue, said second end of said first laser radiation transmission means being disposed at said first end location of said second end of said tubular member, and second laser radiation transmission means having a first end and a second end and being continuous therebetween so that laser radiation can be uninterruptedly transmitted therebetween, said second end of said second laser radiation transmission means being disposed at said second end location of said second end of said tubular member so that laser radiation can be transmitted across said gap between said first and second end locations at said second end of said tubular member.

22. The laser knife of claim 21 wherein said first laser radiation transmission means and said second laser radiation transmission means comprise a plurality of fiber optic members.

23. The laser knife of claim 21 wherein said second end of said tubular member includes a non-linear end portion, said second end of said first laser radiation means being disposed at a first point on said non-linear end portion of said tubular member, and said second end of said second laser radiation transmission means being disposed at a second point on said non-linear end portion of said tubular member.

24. The laser knife of claim 23 wherein said second point on said non-linear end portion of said tubular member is located proximate to said second end of said tubular member and said first point on said non-linear end portion of said tubular member is located distal from said second end of said tubular member.

25. The laser knife of claim 24 wherein said non-linear end portion of said tubular member is arcuate.

26. The laser knife of claim 23 wherein said non-linear end portion of said tubular member comprises a V-shaped end portion including two ends, said second point on said non-linear end portion of said tubular member being located at one of said ends of said V-shaped portion of said tubular member and said first point on said non-linear end portion of said tubular member being located at said second end of said V-shaped portion of said tubular member.

27. The laser knife of claim 21 including prism means associated with both said first laser radiation transmission means and said second laser radiation transmission means for mounting said first and second laser radiation transmission means in optical alignment with each other.

28. A laser knife comprising a tubular member adapted to be inserted into the forceps channel of an endoscope, said tubular member including a V-shaped end portion including two ends, laser radiation transmission means having a first end and a second end, said laser radiation transmission means being disposed within said tubular member for conveying laser radiation therethrough so that laser radiation can be conveyed from said first end of said laser radiation transmission means to be emitted from said second end of said laser radiation transmission means, and acceptor means carried by said tubular member, said second end of said laser radiation transmission means being disposed at one of said ends of said V-shaped end portion of said tubular member, and said acceptor means being disposed at said other end of said V-shaped end portion of said tubular member, said acceptor means being disposed in optical alignment with said second end of said laser radiation transmission means for accepting laser radiation emitted from said second end of said laser radiation transmission means; and a laser oscillator providing laser radiation to the first end of said laser radiation transmission means at a level sufficient to cauterize human tissue.

29. A laser knife comprising a tubular member adapted to be inserted into the forceps channel of an endoscope, laser radiation transmission means having a first end and a second end, said laser radiation transmission means being disposed within said tubular member for conveying laser radiation therethrough so that laser radiation can be conveyed from said first end of said laser radiation transmission means to be emitted from said second end of said laser radiation transmission means, acceptor means carried by said tubular member, and retainer means carrying said laser radiation transmission means, said retainer means being axially movable in first and second opposite directions within said tubular member so that said second end of said laser radiation transmission means can be moved between first and second positions by respectively axially moving said retainer means in said first and second directions in said tubular member, said first postion being proximate to said acceptor means and said second position being distal from said acceptor means, so that when said seecond end of said laser radiation transmission means and said acceptor means are in said proximate position with respect to each other, they can hold an affected part therebetween, said acceptor means being disposed in optical alignment with said second end of said laser radiation transmission means for accepting laser radiation emitted from said second end of said laser radiation transmission means.

30. The laser knife of claim 29 including displacing means for axially moving said retainer means with respect to said tubular member.

31. The laser knife of claim 30 wherein said displacing means includes a first arm affixed to said tubular member and a second arm affixed to said retainer means, said first and second arms being pivotally connected to each other.

32. The laser knife of claim 29 wherein said retainer means also carries said acceptor means.

33. A laser knife comprising a tubular member adapted to be inserted into the forceps channel of an endoscope, laser radiation transmission means having a first end and a second end, said laser radiation transmission means being disposed within said tubular member for conveying laser radiation therethrough so that laser radiation can be conveyed from said first end of said laser radiation transmission means to be emitted from said second end of said laser radiation transmission means, acceptor means carried by said tubular member, retainer means carrying said laser radiation transmission means and said acceptor means, said retainer means being axially movable in first and second directions within said tubular member, and first and second holding members carried by said retainer means, said first holding member being associated with said laser radiation transmission means and said second holding member being associated with said acceptor means, said first and second holding members being biased apart so that when said retainer means is axially moved in said second direction, said tubular member causes said first and second holding members to be urged together against said bias, said acceptor means being disposed in optical alignment with said second end of said laser radiation transmission means for accepting laser radiation emitted from said second end of said laser radiation transmission means.

34. The laser knife of claim 33 including a laser oscillator for supplying laser radiation to said laser radiation transmission means.

35. The laser knife of claim 33 wherein said laser radiation transmission means comprises a first laser radiation transmission means and said acceptor means comprises a second laser radiation transmission means for conveying said accepted laser radiation, said second laser radiation transmission means having a first end for accepting said laser radiation and a second end, and including means associated with said first end of said tubular member for discharging laser radiation emitted from said first end of said tubular member.

36. A laser knife comprising a tubular member adapted to be inserted into the forceps channel of an endoscope, said tubular member having a first end and a second end, said second end of said tubular member including a V-shaped end portion including two ends, first laser radiation transmission means having a first end and a second end, said first laser radiation transmission means being disposed within said tubular member for conveying laser radiation therethrough so that laser radiation can be conveyed from either said first end or said second end of said first laser radiation transmission means to be emitted from either said second end or said first end, respectively, of said first laser radiation transmission means, second laser radiation transmission means having a first end and a second end, said second laser radiation transmission means being disposed within said tubular member for conveying laser radiation therethrough so that laser radiation can be conveyed from either said first end or said second end of said second laser radiation transmission means to be emitted from either said second end or said first end, respectively, of said second laser radiation transmission means, said second end of said first laser radiation transmission means being disposed at one of said ends of said V-shaped portion of said tubular member, and said second end of said second laser radiation transmission means being disposed at said other end of said V-shaped portion of said tubular member, said second laser radiation transmission means being disposed in optical alignment with said second end of said first laser radiation transmission means so that laser radiation from either said first or said second laser radiation transmission means can be accepted by said second or said first laser radiation transmission means, respectively; and a laser oscillator for coupling laser radiation to the first end of one of said first and second laser radiation transmission means of a level sufficient to cauterize human tissue.

* * * * *

UNITED STATES PATENT AND TRADEMARK OFFICE
CERTIFICATE OF CORRECTION

PATENT NO. : 4,266,547
DATED : May 12, 1981
INVENTOR(S) : OSAMU KOMIYA

It is certified that error appears in the above—identified patent and that said Letters Patent is hereby corrected as shown below:

Column 1, line 6, after "utilizes" insert --laser--.

Column 9, on lines 40 and 41, change "rotation" to --radiation--.

Column 9, line 30, change "v-" to --V- --.

Signed and Sealed this

Twenty-fifth Day of August 1981

[SEAL]

Attest:

Attesting Officer

GERALD J. MOSSINGHOFF

Commissioner of Patents and Trademarks